United States Patent
Nayak

(10) Patent No.: US 11,806,516 B2
(45) Date of Patent: Nov. 7, 2023

(54) DRUG DELIVERY DEVICE AND CHARGING DEVICE

(71) Applicant: SANOFI, Paris (FR)

(72) Inventor: Atul Nayak, Bridgewater, NJ (US)

(73) Assignee: Sanofi, Paris (FR)

( * ) Notice: Subject to any disclaimer, the term of this patent is extended or adjusted under 35 U.S.C. 154(b) by 359 days.

(21) Appl. No.: 16/772,441

(22) PCT Filed: Dec. 17, 2018

(86) PCT No.: PCT/EP2018/085115
§ 371 (c)(1),
(2) Date: Jun. 12, 2020

(87) PCT Pub. No.: WO2019/121451
PCT Pub. Date: Jun. 27, 2019

(65) Prior Publication Data
US 2021/0077748 A1    Mar. 18, 2021

(30) Foreign Application Priority Data
Dec. 18, 2017  (EP) ..................................... 17306809

(51) Int. Cl.
*A61M 5/44*    (2006.01)

(52) U.S. Cl.
CPC ..... *A61M 5/445* (2013.01); *A61M 2205/3368* (2013.01); *A61M 2205/3553* (2013.01);
(Continued)

(58) Field of Classification Search
CPC .. A61M 2205/8243; A61M 2205/3368; A61M 2205/368; A61M 5/44;
(Continued)

(56) References Cited

U.S. PATENT DOCUMENTS

| | | |
|---|---|---|
| 2006/0247737 A1 | 11/2006 | Olson et al. |
| 2007/0270744 A1 | 11/2007 | Dacquay et al. |

(Continued)

FOREIGN PATENT DOCUMENTS

| | | |
|---|---|---|
| CN | 102105186 | 6/2011 |
| CN | 203090273 | 7/2013 |

(Continued)

OTHER PUBLICATIONS

PCT International Preliminary Report on Patentability in International Appln. No. PCT/EP2018/085115, dated Jun. 23, 2020, 7 pages.

(Continued)

*Primary Examiner* — Emily L Schmidt
(74) *Attorney, Agent, or Firm* — Fish & Richardson P.C.

(57) ABSTRACT

A drug delivery device for delivering a medicament includes a housing arranged to contain a container, a receiver coil, and an energy storage unit. The receiver coil is arranged to receive energy from a transmitter coil by electromagnetic induction. The energy storage unit is arranged to be charged by at least a portion of the energy received by the receiver coil. At least a portion of the energy received by the receiver coil is converted to heat energy. The receiver coil is arranged in the drug delivery device to transfer the heat energy to the container to heat medicament contained in the container. A system comprising the drug delivery device is also disclosed.

18 Claims, 4 Drawing Sheets

(52) U.S. Cl.
CPC . *A61M 2205/368* (2013.01); *A61M 2205/581* (2013.01); *A61M 2205/582* (2013.01); *A61M 2205/583* (2013.01); *A61M 2205/8243* (2013.01)

(58) Field of Classification Search
CPC .... A61M 2005/14553; A61M 5/14546; A61M 5/14566; A61M 2005/14573
See application file for complete search history.

(56) References Cited

U.S. PATENT DOCUMENTS

| | | |
|---|---|---|
| 2011/0172525 A1 | 7/2011 | Neer |
| 2012/0029349 A1* | 2/2012 | Bruce ............... A61M 5/14566 600/432 |
| 2012/0078181 A1 | 3/2012 | Smith et al. |
| 2012/0089114 A1* | 4/2012 | Hemond ................ A61M 5/46 604/500 |
| 2013/0109987 A1* | 5/2013 | Kunis ...................... A61F 2/88 606/41 |
| 2013/0313249 A1* | 11/2013 | Cregut .................. B60L 53/122 219/618 |
| 2015/0202456 A1* | 7/2015 | Andersen ............. A61K 38/164 604/20 |
| 2018/0126177 A1* | 5/2018 | Scott ..................... A61F 7/0085 |

FOREIGN PATENT DOCUMENTS

| | | |
|---|---|---|
| JP | 2010-535040 | 11/2010 |
| JP | 2012-510868 | 5/2012 |
| JP | 2017-522992 | 8/2017 |
| WO | WO 2010/065726 | 6/2010 |
| WO | WO 2014/139535 | 9/2014 |
| WO | WO 2016/022688 | 2/2016 |
| WO | WO 2017/054009 | 3/2017 |

OTHER PUBLICATIONS

PCT International Search Report and Written Opinion in International Appln. No. PCT/EP2018/085115, dated Feb. 1, 2019, 9 pages.

* cited by examiner

DRUG DELIVERY DEVICE AND CHARGING DEVICE

CROSS REFERENCE TO RELATED APPLICATIONS

The present application is the national stage entry of International Patent Application No. PCT/EP2018/085115, filed on Dec. 17, 2018, and claims priority to Application No. EP 17306809.9, filed on Dec. 18, 2017, the disclosures of which are incorporated herein by reference.

TECHNICAL FIELD

The present disclosure relates to a drug delivery device and a charging device, in particular, but not exclusively, wherein medicament in the drug delivery device can be heated by electromagnetic induction.

BACKGROUND

Many medicaments require refrigeration while in storage.

SUMMARY

According to a first aspect of the present disclosure, there is provided a drug delivery device for delivering a medicament, the drug delivery device comprising: a housing arranged to contain a container; a receiver coil; and an energy storage unit, wherein the receiver coil is arranged to receive energy from a transmitter coil by electromagnetic induction, wherein the energy storage unit is arranged to be charged by at least a portion of the energy received by the receiver coil, wherein at least a portion of the energy received by the receiver coil is converted to heat energy, and wherein the receiver coil is arranged in the drug delivery device to transfer the heat energy to the container to heat medicament contained in the container.

The drug delivery device may further comprise a resonant circuit, wherein the receiver coil and resonant circuit are arranged to receive the energy from the transmitter coil by resonant inductive coupling.

The drug delivery device may further comprise a sensing unit and an antenna, wherein the sensing unit is arranged to determine a usage parameter of the drug delivery device, and wherein the drug delivery device is arranged to transmit a wireless electromagnetic signal using the antenna, the wireless electromagnetic signal corresponding to the determined usage parameter.

The receiver coil may be a transceiver coil, and the antenna may comprise the transceiver coil.

The drug delivery device may further comprise a temperature sensor, wherein the drug delivery device is arranged to provide an output dependent upon a temperature of the medicament detected by the temperature sensor.

The output may comprise an audio, visual or haptic output.

The output may comprise a wireless electromagnetic signal transmitted using the receiver coil.

The drug delivery device may include a medicament contained in the container.

According to a second aspect of the present disclosure, there is provided a system comprising: drug delivery device as disclosed herein; and a charging device for heating medicament contained in the drug delivery device using electromagnetic induction, the charging device comprising: a driving circuit; and a transmitter coil, wherein the driving circuit is arranged to drive the transmitter coil, wherein the driving circuit and the transmitter coil are arranged to transmit energy to a receiver coil of the drug delivery device by electromagnetic induction, and wherein the receiver coil of the drug delivery device is arranged to receive the energy from the transmitter coil of the charging device and to heat medicament contained in the drug delivery device.

The driving circuit and transmitter coil may be arranged to transmit the energy by resonant inductive coupling.

The charging device may be configured to surround the drug delivery device may be configurable to surround the drug delivery device.

The charging device may be a sleeve, a wrap, a pad or a glove.

The transmitter coil may be a transceiver coil, wherein the transceiver coil is arranged to receive an electromagnetic signal transmitted by the drug delivery device, wherein the electromagnetic signal corresponds to determined usage parameter of the drug delivery device.

The charging device may further comprise an acoustic sensor arranged to detect an acoustic signal output by the drug delivery device, the acoustic signal corresponding to a usage parameter of the drug delivery device.

The charging device may further comprise a temperature sensor arranged to determine a temperature of the drug delivery device when the transmitter coil is transmitting energy to the receiver coil of the drug delivery device.

Discomfort experienced by a patient during injection of the medicament can be reduced by bringing the medicament to ambient temperature or to the body temperature of the patient. Medicaments such as insulin which may be administered using an auto-injector or pen-injector may be allowed to return to room temperature prior to administration so that discomfort experienced by the user of the injector is reduced.

BRIEF DESCRIPTION OF THE FIGURES

Embodiments of the present disclosure will now be described, by way of example only, with reference to the accompanying drawings, in which:

FIG. 5 illustrates a method of using the drug delivery device of FIG. 2 and the charging device of FIG. 3;

FIG. 6 is illustrates a method of using the drug delivery device of FIG. 2 and the charging device of FIG. 3.

Reference will now be made in detail to the embodiments of the present disclosure, examples of which are illustrated in the accompanying drawings, wherein like reference numerals refer to like elements throughout.

DETAILED DESCRIPTION

According to some embodiments of the present disclosure, a drug delivery device for delivering a medicament comprises a housing arranged to contain a container, a receiver coil, and an energy storage unit. The receiver coil is arranged to receive energy from a transmitter coil by electromagnetic induction. The energy storage unit is arranged to be charged by at least a portion of the energy received by the receiver coil. At least a portion of the energy received by the receiver coil is converted to heat energy. The receiver coil is arranged in the drug delivery device to transfer the heat energy to the container to heat medicament contained in the container.

Figure 1A:
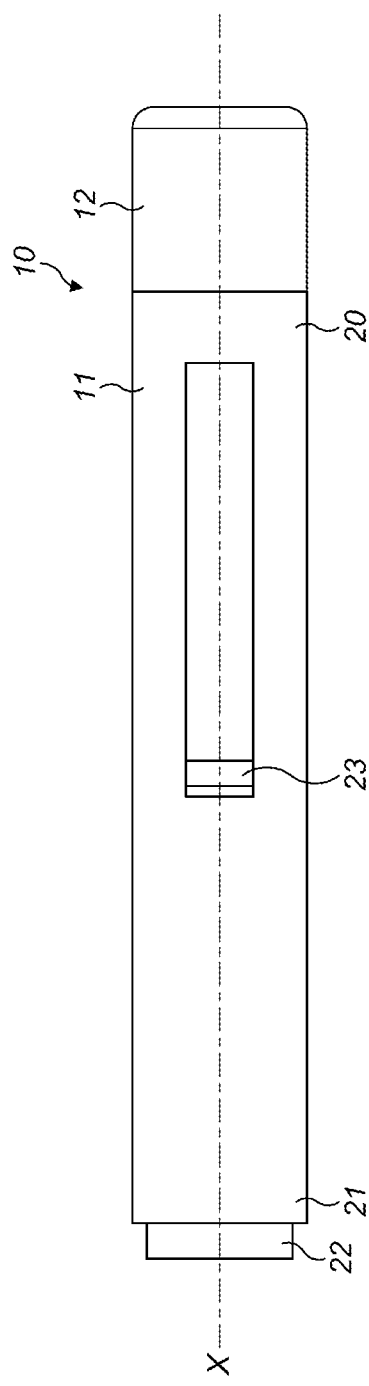
FIGS. 1A and 1B are side-on views of an exemplary drug delivery device according to embodiments of the present disclosure.
Figure 1B:
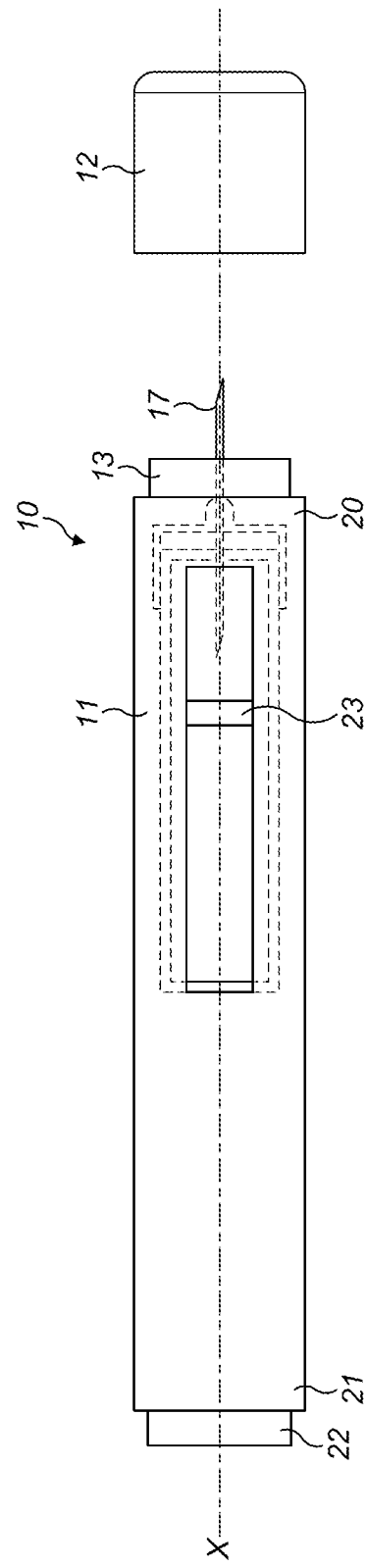

According to some embodiments of the present disclosure, an exemplary drug delivery device 10 is shown in FIGS. 1A & 1B. This drug delivery device 10 may be known as a pen injector or an auto-injector. However other types of drug delivery devices may be used with the present disclosure. The drug delivery device 10 is arranged to contain a container. The container is for containing medicament to be delivered to a patient. The container may be configured to be single-use or reusable. The drug delivery device 10 may comprise the container, or may be configured to have a container inserted prior to medicament administration. Suitable drug delivery devices for the present disclosure include cartridge-based devices, syringes, pen injectors, auto-injectors and the like.

The drug delivery device 10 is configured to inject a medicament into a patient's body. The drug delivery device 10 includes a housing 11 which typically contains a container containing the medicament to be injected (e.g., a syringe or cartridge) and the components required to facilitate one or more steps of the delivery process. The drug delivery device 10 can also include a cap assembly 12 that can be detachably mounted to the housing 11. Typically a user must remove cap 12 from the housing 11 before the drug delivery device 10 can be operated.

As shown, the housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

The drug delivery device 10 can also include a needle sleeve 13 coupled to the housing 11 to permit movement of the sleeve 13 relative to the housing 11. For example, the sleeve 13 can move in a longitudinal direction parallel to longitudinal axis X. Specifically, movement of the sleeve 13 in a proximal direction can permit a needle 17 to extend from the distal region 20 of the housing 11.

Insertion of the needle 17 can occur via several mechanisms. For example, the needle 17 may be fixedly located relative to the housing 11 and initially be located within the extended needle sleeve 13. Proximal movement of the sleeve 13 by placing a distal end of sleeve 13 against a patient's body and moving the housing 11 in a distal direction will uncover the distal end of the needle 17. Such relative movement allows the distal end of the needle 17 to extend into the patient's body. Such insertion is termed "manual" insertion as the needle 17 is manually inserted via the patient's manual movement of the housing 11 relative to the sleeve 13.

Another form of insertion is "automated," whereby the needle 17 moves relative to the housing 11. Such insertion can be triggered by movement of the sleeve 13 or by another form of activation, such as, for example, a button 22. As shown in FIGS. 1A & 1B, the button 22 is located at a proximal end of housing 11. However, in other embodiments, the button 22 could be located on a side of the housing 11.

Other manual or automated features can include drug injection or needle retraction, or both. Injection is the process by which a bung or piston 23 is moved from a proximal location within a syringe (not shown) to a more distal location within the syringe in order to force a medicament from the syringe through the needle 17. In some embodiments, a drive spring (not shown) is under compression before the drug delivery device 10 is activated. A proximal end of the drive spring can be fixed within the proximal region 21 of the housing 11, and a distal end of the drive spring can be configured to apply a compressive force to a proximal surface of the piston 23. Following activation, at least part of the energy stored in the drive spring can be applied to the proximal surface of the piston 23. This compressive force can act on the piston 23 to move it in a distal direction. Such distal movement acts to compress the liquid medicament within the syringe, forcing it out of the needle 17.

Following injection, the needle 17 can be retracted within the sleeve 13 or the housing 11. Retraction can occur when the sleeve 13 moves distally as a user removes the drug delivery device 10 from a patient's body. This can occur as the needle 17 remains fixedly located relative to the housing 11. Once a distal end of the sleeve 13 has moved past a distal end of the needle 17 and the needle 17 is covered, the sleeve 13 can be locked. Such locking can include locking any proximal movement of the sleeve 13 relative to the housing 11.

Another form of needle retraction can occur if the needle 17 is moved relative to the housing 11. Such movement can occur if the syringe within the housing 11 is moved in a proximal direction relative to the housing 11. This proximal movement can be achieved by using a retraction spring (not shown), located in the distal region 20. A compressed retraction spring, when activated, can supply sufficient force to the syringe to move it in a proximal direction. Following sufficient retraction, any relative movement between the needle 17 and the housing 11 can be locked with a locking mechanism. In addition, the button 22 or other components of the drug delivery device can be locked as required.

The drug delivery device 10 may be a handheld injector such as a pen injector. The drug delivery device 10 described in relation to FIGS. 1A and 1B is given by way of example. Other suitable forms of the drug delivery device 10 may be used in accordance with aspects of the present disclosure. For example, the drug delivery device 10 may not have some of the components described in relation to FIGS. 1A and 1B, or may have additional components.

Figure 2:
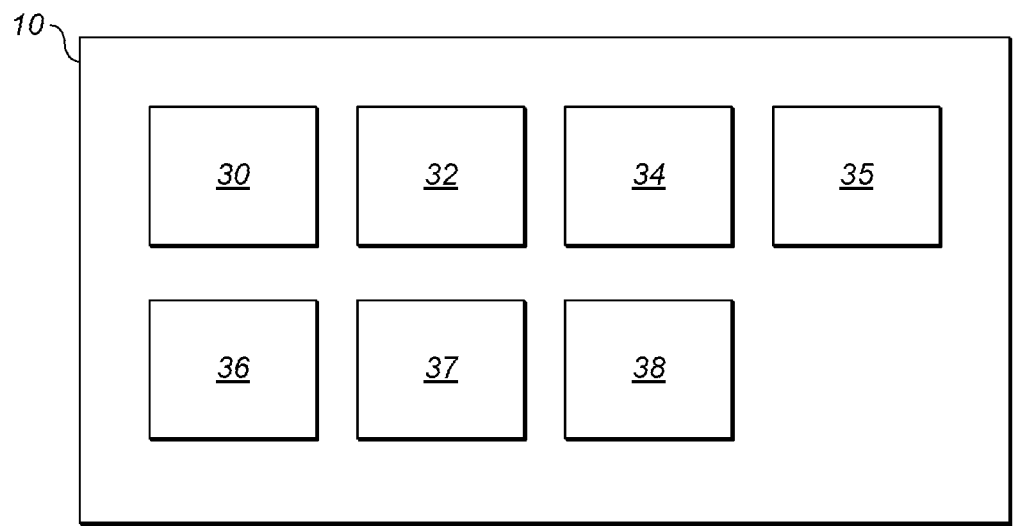
FIG. 2 is a schematic of components with the drug delivery device of FIGS. 1A and 1B.

FIG. 2 is a schematic illustration of components within the drug delivery device 10, in particular components of a circuit within the drug delivery device 10.

The drug delivery device 10 contains a receiver coil 30 and an energy storage unit 32. The receiver coil 30 is arranged to receive energy from a corresponding transmitter coil (not shown) contained in a charging device by electromagnetic induction, such as resonant inductive coupling. At least a portion of the energy received by the receiver coil 30 is used to charge the energy storage unit 32. The energy storage unit 32 may then supply power to electrical components of the drug delivery device 10 such as a control unit 34, a sensing unit 35, a temperature sensor 36, or an output device 37. The energy storage unit 32 may comprise a capacitor or a cell.

As energy is transferred from the transmitter coil of a charging device to the receiver coil 30 of the drug delivery device 10, inefficiency in the coupling of the transmitter coil and the receiver coil 30 leads to heat being generated by the receiver coil 30. Aspects of the present disclosure may allow this heat to be harvested and used. In particular, the receiver coil 30 is arranged in the drug delivery device 10 to transfer the heat energy to the container to heat medicament contained in the container. The receiver coil 30 may be located in the drug delivery device 10 adjacent the container so that the heat is more efficiently transferred to the medicament contained in the container. In some examples, the receiver coil 30 may be located on a surface of the container, such as the outer surface, or may be embedded within the walls of the container. The receiver coil 30 may be flexible so that it can be more easily applied to contours of the container. Heating the medicament contained in the container of the drug delivery device 10 using heat energy generated by electromagnetic induction (such as resonant inductive coupling) can reduce the discomfort experienced by a patient to whom the medicament is being delivered.

The control unit 34 may control various operations of the drug delivery device 10. For example, the control unit 34 may receive electrical inputs from the receiver coil 30, the sensing unit 35, and/or the temperature sensor 36. The control unit 34 may process one or more electrical inputs and provide a corresponding electrical output to another component, for example the receiver coil 30, the resonant circuit 38, or the output device 37. The control unit 34 may comprise one or more processors, one or more logic units, or the like.

The sensing unit 35 may be arranged to determine one or more usage parameters of the drug delivery device 10. The usage parameters may include a number of drug delivery cycles, an amount of medicament delivered, a time of drug delivery, or the like. The drug delivery device 10 may be arranged to transmit a wireless electromagnetic signal using an antenna of the drug delivery device 10, the wireless electromagnetic signal corresponding to the one or more determined usage parameters. An apparatus such as charging device 40, described with reference to FIG. 3, may be configured to receive and process the wireless electromagnetic signal in order to determine the one or more usage parameters of the drug delivery device 10. In some examples, the receiver coil 30 may be a transceiver coil. The antenna may therefore comprise the transceiver coil.

The drug delivery device 10 may comprise a temperature sensor 36 for detecting a temperature, such as the temperature of the medicament contained within the container of the drug delivery device 10. The temperature sensor 36 may therefore be located adjacent the container such that it is in close proximity to the medicament, improving the accuracy of the temperature measurement. The temperature sensor 36 may be located on a surface of the container. A flexible temperature sensor 36 may be used such that the temperature sensor 36 can be adhered to a surface of the container.

The drug delivery device 10 may also comprise an output device 37. The output device 37 may be configured to output one or more of an audio, visual or haptic output in response to an electrical signal output by the control unit 34. For example, the output device 37 may comprise one or more speakers, light emitting diodes, displays or vibrating units.

The drug delivery device 10 may comprise a resonant circuit 38 electrically coupled to the receiver coil 30 such that energy can be transferred to the receiver coil 30 from the transmitter coil of the charging device by resonant inductive coupling.

Figure 3:
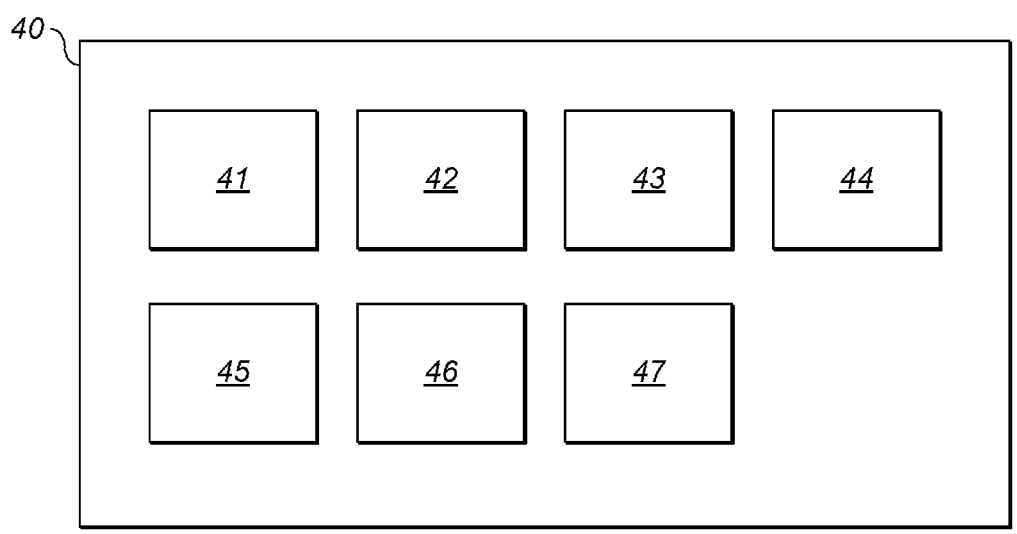
FIG. 3 is a schematic of components within a charging device for transferring energy to the drug delivery device of FIG. 2.

FIG. 3 is a schematic illustration of a charging device 40 according to aspects of the present disclosure. The charging device 40 is for heating the medicament contained in the drug delivery device 10 using electromagnetic induction.

The charging device 40 comprises a power supply 41, a transmitter coil 42 and a driving circuit 43. The power supply 41 is configured to supply power to the various electrical components of the charging device 40. The power supply 41 may comprise a battery, or a connector for connecting the charging device 40 to a mains supply.

The driving circuit 43 drives the transmitter coil 42 to generate a time-varying magnetic field. The time-varying magnetic field induces a voltage across the receiver coil 30 of the drug delivery device 10 by electromagnetic induction. Energy is therefore transferred from the transmitter coil 42 to the receiver coil 30.

In some examples, the charging device 40 further comprises a temperature sensor 44. The temperature sensor 44 is arranged to determine a temperature of the drug delivery device 10 when the transmitter coil 42 is transmitting energy to the receiver coil 30 of the drug delivery device 10. For example, the temperature sensor 44 may be arranged within the charging device 40 such that it is adjacent the drug delivery device 10 when the drug delivery device is brought into proximity with the charging device 40.

The charging device 40 may comprise a sensing unit 47 arranged to determine one or more usage parameters of the drug delivery device 10. The usage parameters may include a number of drug delivery cycles, an amount of medicament delivered, a time of drug delivery, or the like. The sensing unit 47 may comprise an acoustic sensing unit, wherein the acoustic sensing unit is configured to detect an acoustic signal output by the drug delivery device 10, and to determine the one or more usage parameters based on the detected acoustic signal.

The charging device 40 may comprise a control unit 45, which may control various operations of the charging device 40. For example, the control unit 45 may receive electrical inputs from the transmitter coil 42, the sensing unit 47, the power supply 41, and/or the temperature sensor 44. The control unit 45 may process one or more electrical inputs and provide a corresponding electrical output to a component, for example the transmitter coil 42, or an output device 46. The control unit 45 may comprise one or more processors, one or more logic units, or the like.

In a similar manner to the drug delivery device 10, the output device 46 of the charging device 40 may output one or more of an audio, visual or haptic output in response to an electrical signal output by the control unit 45. For example, the output device 46 may comprise one or more speakers, light emitting diodes, displays or vibrating units. The output may be dependent upon the temperature of the medicament in the drug delivery device 10 as determined by the temperature sensor 36 of the drug delivery device 10 or the temperature sensor 44 of the charging device 40.

One or more electrical components of the charging device 40 may be flexible at least in part. For example the transmitter coil 42 may be flexible. Various electronics of the charging device 40 may be produced by screen printing techniques. The use of flexible electronics where possible can be beneficial in that it allows the charging device 40 to have a variety of form factors, such as those discussed below with relation to FIGS. 4A, 4B and 4C.

Figure 4A:
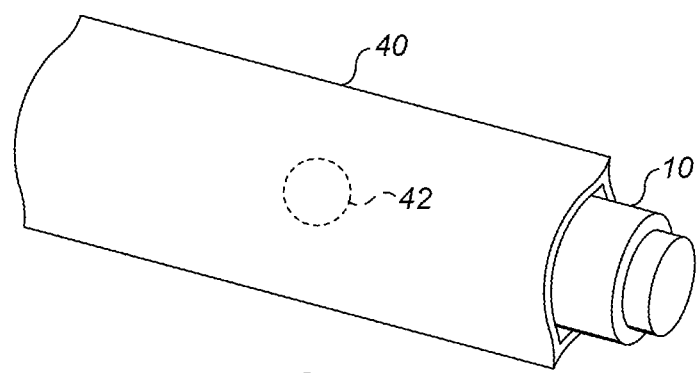
FIG. 4A is an illustration of an embodiment wherein the charging device of FIG. 3 is a sleeve.
Figure 4B:
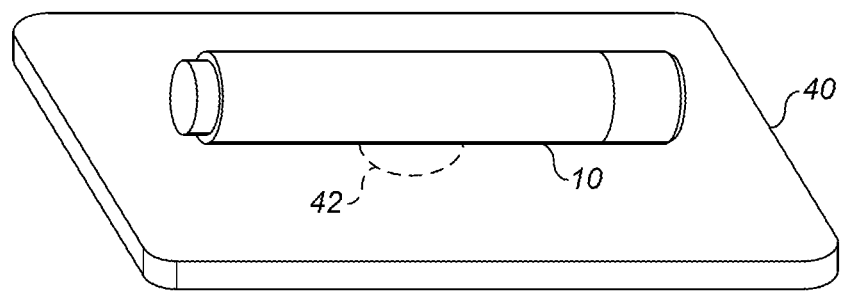
FIG. 4B is an illustration of an embodiment wherein the charging device of FIG. 3 is a pad.
Figure 4C:
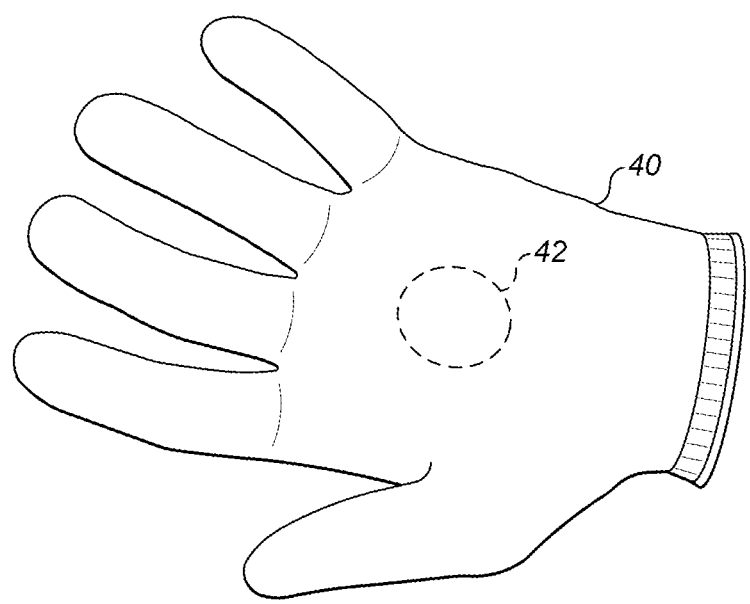
FIG. 4C is an illustration of an embodiment wherein the charging device of FIG. 3 is a glove.

FIGS. 4A, 4B and 4C illustrate various embodiments of the charging device 40. In each of the embodiments, the charging device 40 may be configured to surround the drug delivery device 10, or is configurable to surround the drug delivery device 10.

Where the charging device 40 is configurable to surround the drug delivery device 10, the charging device 40 may have a first physical configuration in which it cannot surround the drug delivery device 10, and a second physical configuration in which it can surround the drug delivery device 10, wherein the charging device 40 can be changed between the first physical configuration and second physical configuration. The change between the first and second physical configurations may be reversible.

FIG. 4A shows an embodiment wherein the charging device 40 is a sleeve, such as a pouch. The drug delivery device 10 can be inserted into the sleeve such that the sleeve surrounds the drug delivery device 10 at least partially.

The dotted circle indicates an approximate location of the transmitter coil 42 in the charging device 40. The transmitter coil 42 is located in the charging device 40 such that it corresponds to the location of the receiver coil 30 of the drug delivery device 10 when the drug delivery device 10 is surrounded by the charging device 40. In other words, the transmitter coil 42 is located such that it is adjacent the receiver coil 30 when the drug delivery device 10 is inserted into the sleeve, so that electromagnetic induction may occur between the transmitter coil 42 and receiver coil 30.

In some examples, the charging device 40 may be a wrap, wherein the wrap is configurable to surround the drug delivery device 10. For example, the charging device may be a flexible sheet that can be wrapped around the drug delivery device 10 before use of the drug delivery device 10. The wrap may have a fastener to keep the wrap in place when surrounding the drug delivery device 10. For example, the fastener may comprise a hook and loop fastener, snap fastener, zip, adhesive, or another suitable fastening means. The fastener may be releasable to allow for re-use of the wrap.

FIG. 4B shows an embodiment wherein the charging device 40 is a pad. The pad may be rigid or flexible. The pad is configured such that the drug delivery device 10 may be placed rested on a surface of the pad.

Again, the dotted circle indicates an approximate location of the transmitter coil 42 in the charging device 40. The transmitter coil 42 is located in the charging device 40 such that it corresponds to the location of the receiver coil 30 of the drug delivery device 10 when the drug delivery device 10 is placed on (or otherwise brought into close proximity with) the charging device 40. In other words, the transmitter coil 42 is located such that it is adjacent the receiver coil 30 when the drug delivery device 10 is positioned on the pad, so that electromagnetic induction may occur between the transmitter coil 42 and receiver coil 30.

FIG. 4C shows an embodiment wherein the device is a glove. The transmitter coil may be located in the glove such that it can inductively couple to the receiver coil of the drug delivery device when a user wearing the glove is holding the drug delivery device with their gloved hand. For example, the transmitter coil may be located at the palm of the glove. The transmitter coil may be located on an outer surface or inner surface of the glove, or may be contained within the material of the glove.

Again, the dotted circle indicates an approximate location of the transmitter coil 42 in the charging device 40. The transmitter coil 42 is located in the charging device 40 such that it corresponds to the location of the receiver coil 30 of the drug delivery device 10 when the drug delivery device 10 is held in (or otherwise brought into close proximity with) the charging device 40. In other words, the transmitter coil 42 is located such that it is adjacent the receiver coil 30 when the drug delivery device 10 is held in the glove, so that electromagnetic induction may occur between the transmitter coil 42 and receiver coil 30.

In each of the above embodiments, the charging device 40 may have an anti-slip outer surface. This may ensure that the charging device 40 can be easily and securely held by a user, in the case of the charging device 40 being a sleeve, or that the drug delivery device 10 can be easily and securely held in the charging device 40, in the case of the charging device 40 being a glove.

The charging device 40 may transparent or translucent at least in part. In embodiments wherein the charging device 40 is a sleeve or wrap, this may enable a user to view the drug delivery device 10 through the charging device 40. For example, the user may be able to view a display of the drug delivery device 10 through the charging device 40, or may be able to view an amount of medicament remaining in the drug delivery device 10.

FIG. 5 illustrates an exemplary method of using the device and drug delivery device.

In a first step 510, the drug delivery device 10 is brought into proximity of the charging device 40. In other words, the drug delivery device 10 and charging device 40 are brought together such that the transmitter coil of the charging device 40 and the receiver coil of the drug delivery device can be inductively coupled. If the device is a pouch, this may involve inserting the drug delivery device into the pouch such that at least part of the drug delivery device is contained within the pouch. If the device is a wrap, first step 510 may involve wrapping the wrap around the drug delivery device. If the device is a glove, first step 510 may involve holding the drug delivery in the glove.

In a second step 520, energy is transmitted from the transmitter coil of the device to the receiver coil of the drug delivery device by electromagnetic induction. The driving circuit of the device drives the transmitter coil so that a time-varying magnetic field is generated. The time-varying magnetic field induces a potential difference across the receiver coil of the drug delivery device. Energy is therefore transferred from the transmitter coil to the receiver coil. At least a part of the energy transferred to the receiver coil may be used to charge the energy storage unit of the drug delivery device. The energy transferred from the transmitter coil to the receiver coil may be used to supply power to one or more electrical components of the drug delivery device. Some of the energy transferred from the transmitter coil to the receiver coil is converted to heat energy. This heat energy is transferred to the medicament contained in the container of the drug delivery device such that the medicament is heated.

Once the medicament has reached a desired temperature, in some cases as determined by temperature sensor 36 or temperature sensor 44, the drug delivery device 10 may be separated from the charging device 40. For example where the charging device 40 is a sleeve, the drug delivery device 10 may be removed from the sleeve. Where the charging device 40 is a wrap, the charging device 40 may be unwrapped from around the drug delivery device 10. The drug delivery device 10 may then be used to perform an injection. In some examples, the charging device 40 and drug delivery device 10 are not separated before performing an injection. For example where the charging device 40 is a sleeve, the drug delivery device 10 may remain in the sleeve during drug delivery. Where the charging device 40 is a wrap, the charging device 40 may remain wrapped around the drug delivery device 10 during drug delivery.

FIG. 6 illustrates a further exemplary method of using the device and drug delivery device.

In step 610, the drug delivery device 10 is brought into proximity of the charging device 40, in a similar manner to step 510 of FIG. 5.

In step 620, the charging device 40 detects that it is in proximity to the drug delivery device. This may be achieved by the charging device 40 detecting a change in capacitance or resonance within the charging device 40.

In step 630, and in response to detection that the charging device 40 is in proximity to the drug delivery device 10, the device transmits a burst signal to the drug delivery device using the transmitter coil.

In step 640, the receiver coil of the drug delivery device receives the burst signal from the charging device 40. The control unit of the drug delivery device detects the burst signal and awakens the drug delivery device from a standby state.

In optional step 650, the drug delivery device transmits a signal to the charging device indicating at least one of an identification of the drug delivery device and a signal strength status. The signal may be transmitted wirelessly using an antenna of the drug delivery device. In some examples, the receiver coil of the drug delivery device is a transceiver coil, and the antenna comprises the transceiver coil. The signal may be received by the transmitter coil of the charging device 40, or another coil of the charging device 40.

In step 660, the driving circuit of the charging device 40 drives the transmitter coil to transmit energy from the transmitter coil to the receiver coil of the drug delivery device, in a similar manner as discussed with respect to step 520 of FIG. 5. In the process of charging the energy storage unit of the drug delivery device, the transmitter coil of the device also causes the generation of heat at the receiver coil of the drug delivery device. This generated heat is used to heat medicament contained in the container of the drug delivery device, for example to bring the medicament to ambient temperature, or body temperature.

In optional step 670, the temperature sensor of the drug delivery device or the temperature sensor of the charging device 40 determines that the temperature of the medicament in the drug delivery device has reached a threshold temperature.

In optional step 680, in response to determining that the temperature of the medicament in the drug delivery device has reached a threshold temperature, the driving circuit may stop driving the transmitter coil or may modify the manner in which the transmitter coil is driven such that energy transfer between the transmitter coil and the receiver coil is stopped or reduced. Heat production at the receiver coil is therefore stopped or reduced, thereby stopping or reducing further heating of the medicament.

Where the temperature sensor in the charging device 40 is used to determine that the temperature of the medicament in the drug delivery device has reached a threshold temperature, the control unit may send an electrical signal to the driving circuit to stop the driving circuit driving the transmitter coil or modify the manner in which the transmitter coil is driven.

Where the temperature sensor in the drug delivery device is used to determine that the temperature of the medicament in the drug delivery device has reached a threshold temperature, the drug delivery device may provide an output dependent upon the temperature of the medicament detected by the temperature sensor. In particular, the control unit of the drug delivery device may cause said output to be provided. The output may comprise a wireless electromagnetic signal transmitted using the receiver coil. The signal may be received by the transmitter coil of the charging device 40, or another coil. It is this signal that may be used by the charging device 40 to determine that the driving circuit should be stopped or modified.

In optional step 690, in response to determining that the temperature of the medicament in the drug delivery device has reached a threshold temperature, an audio, visual or haptic output may be provided by the drug delivery device or the charging device 40, for example using output device 37 or output device 46. For example, in response to determining that the medicament in the drug delivery device has reached a threshold temperature, a light emitting diode of the drug delivery device or charging device 40 may be illuminated.

According to some embodiments of the present disclosure, there is also provided a system comprising a drug delivery device 10 according to the present disclosure and a charging device 40 according to the present disclosure. The driving circuit of the charging device is arranged to drive the transmitter coil of the charging device. The driving circuit and the transmitter coil are arranged to transmit energy to the receiver coil of the drug delivery device by electromagnetic induction, and the receiver coil of the drug delivery device is arranged to receive the energy from the transmitter coil of the charging device and to heat medicament contained in the drug delivery device.

As discussed in relation to FIG. 5, the charging device 40 and drug delivery device 10 may or may not be separated before performing an injection or other form of drug delivery.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A drug delivery device for delivering a medicament, the drug delivery device comprising:
   a housing arranged to contain a container;
   a drive component arranged within the housing of the drug delivery device and configured to move a piston of the container to dispense medicament from the container during a medicament delivery process;
   a receiver coil; and
   an energy storage unit,
   wherein the receiver coil is arranged to receive energy by electromagnetic induction from a transmitter coil of a charging device when the charging device is brought into proximity with the drug delivery device during a charging process,
   wherein the drug delivery device is configured to perform the medicament delivery process while the charging device is separated from the drug delivery device,
   wherein the energy storage unit is arranged to be charged by at least a portion of the energy received by the receiver coil,
   wherein at least a portion of the energy received by the receiver coil is converted by the receiver coil itself to heat energy at the receiver coil, and
   wherein the receiver coil is arranged in the drug delivery device to transfer the heat energy to the container to heat medicament contained in the container.

2. The drug delivery device of claim 1, wherein the receiver coil is located in the drug delivery device adjacent the container.

3. The drug delivery device of claim 1, wherein the drug delivery device comprises the container and the receiver coil is located on a surface of the container.

4. The drug delivery device of claim 1, wherein the drug delivery device comprises the container and the receiver coil is embedded within one or more walls of the container.

5. The drug delivery device of claim 1, further comprising a resonant circuit, wherein the receiver coil and resonant circuit are arranged to receive the energy from the transmitter coil by resonant inductive coupling.

6. The drug delivery device of claim 1, further comprising a sensing unit and an antenna, wherein the sensing unit is arranged to determine a usage parameter of the drug delivery device, and wherein the drug delivery device is arranged to transmit a wireless electromagnetic signal using the antenna, the wireless electromagnetic signal corresponding to the determined usage parameter.

7. The drug delivery device of claim 6, wherein the receiver coil is a transceiver coil, and wherein the antenna comprises the transceiver coil.

8. The drug delivery device of claim 1, further comprising a temperature sensor, wherein the drug delivery device is arranged to provide an output dependent upon a temperature of the medicament detected by the temperature sensor.

9. The drug delivery device of claim 8, wherein the output comprises an audio, visual or haptic output.

10. The drug delivery device of claim 8, wherein the output comprises a wireless electromagnetic signal transmitted using the receiver coil.

11. The drug delivery device of claim 1, wherein the drug delivery device comprises the container and the container contains a medicament.

12. A system comprising:
   a drug delivery device comprising:
      a housing arranged to contain a container;
      a drive component arranged within the housing of the drug delivery device and configured to move a piston of the container to dispense medicament from the container during a medicament delivery process;
      a receiver coil; and
      an energy storage unit,
      wherein the receiver coil is arranged to receive energy by electromagnetic induction from a transmitter coil of a charging device when the charging device is brought into proximity with the drug delivery device during a charging process, wherein the drug delivery device is configured to perform the medicament delivery process while the charging device is separated from the drug delivery device, wherein the energy storage unit is arranged to be charged by at least a portion of the energy received by the receiver coil, wherein at least a portion of the energy received by the receiver coil is converted by the receiver coil itself to heat energy at the receiver coil, and wherein the receiver coil is arranged in the drug delivery device to transfer the heat energy to the container to heat medicament contained in the container; and the charging device for heating medicament contained in the drug delivery device using electromagnetic induction, the charging device comprising:

a driving circuit; and the transmitter coil, wherein the driving circuit is arranged to drive the transmitter coil, wherein the driving circuit and the transmitter coil are arranged to transmit energy to a receiver coil of the drug delivery device by electromagnetic induction, and wherein the receiver coil of the drug delivery device is arranged to receive the energy from the transmitter coil of the charging device and to heat medicament contained in the drug delivery device.

13. The system of claim 12, wherein the driving circuit and transmitter coil are arranged to transmit the energy by resonant inductive coupling.

14. The system according to claim 12, wherein the charging device is configured to surround the drug delivery device or is configurable to surround the drug delivery device.

15. The system according to claim 14, wherein the charging device is a sleeve, a wrap, a pad or a glove.

16. The system according to claim 12, wherein the transmitter coil is a transceiver coil, wherein the transceiver coil is arranged to receive an electromagnetic signal transmitted by the drug delivery device, wherein the electromagnetic signal corresponds to determined usage parameter of the drug delivery device.

17. The system according to claim 12, wherein the charging device further comprises an acoustic sensor arranged to detect an acoustic signal output by the drug delivery device, the acoustic signal corresponding to a usage parameter of the drug delivery device.

18. The system according to claim 12, wherein the charging device further comprises a temperature sensor arranged to determine a temperature of the drug delivery device when the transmitter coil is transmitting energy to the receiver coil of the drug delivery device.

* * * * *